US006193891B1

(12) United States Patent
Kent et al.

(10) Patent No.: US 6,193,891 B1
(45) Date of Patent: Feb. 27, 2001

(54) METHODS FOR THE SELECTIVE SEPARATION OF ORGANIC COMPONENTS FROM BIOLOGICAL FLUIDS

(75) Inventors: Randall S. Kent, Thousand Oaks, CA (US); William N. Drohan, Springfield, VA (US)

(73) Assignee: American National Red Cross, Washington, DC (US)

(*) Notice: Subject to any disclaimer, the term of this patent is extended or adjusted under 35 U.S.C. 154(b) by 0 days.

(21) Appl. No.: 08/765,101

(22) PCT Filed: Dec. 20, 1996

(86) PCT No.: PCT/US96/20034

§ 371 Date: Dec. 20, 1996

§ 102(e) Date: Dec. 20, 1996

(87) PCT Pub. No.: WO97/23599

PCT Pub. Date: Jul. 3, 1997

Related U.S. Application Data

(60) Provisional application No. 60/021,545, filed on Jul. 10, 1996.

(51) Int. Cl.$^7$ .................................................. B01D 15/00

(52) U.S. Cl. ........................ 210/645; 210/502.1; 210/660; 210/663; 210/690; 423/331; 424/693; 604/4.01

(58) Field of Search ............................... 210/263, 502.1, 210/634, 648, 660, 663, 670, 679, 691, 806, 667, 690, 645, 767; 604/4–6; 423/326, 327.1, 331; 106/970

(56) References Cited

U.S. PATENT DOCUMENTS

| | | |
|---|---|---|
| 2,539,397 | 1/1951 | Bottoms et al. . |
| 3,099,626 | 7/1963 | Riede . |
| 3,989,622 | 11/1976 | Marantz et al. . |
| 4,112,129 | 9/1978 | Duensing et al. . |
| 4,399,164 | 8/1983 | Lauck et al. . |
| 4,421,684 * | 12/1983 | Nakashima et al. ................ 210/691 |
| 4,472,303 * | 9/1984 | Tanihara et al. .................... 210/691 |
| 4,775,483 * | 10/1988 | Mookerjea et al. ................. 210/691 |
| 5,037,649 * | 8/1991 | Balint et al. ....................... 210/691 |
| 5,252,762 | 10/1993 | Denton . |
| 6,008,040 * | 12/1999 | Datar ................................. 210/767 |

FOREIGN PATENT DOCUMENTS

| | | |
|---|---|---|
| 0 507 217 | 10/1992 | (EP) . |
| 0 717 928 | 6/1996 | (EP) . |
| 2 561 074 | 9/1985 | (FR) . |
| 53-27491 * | 3/1978 | (JP) ................................... 210/667 |
| 55-45458 * | 3/1980 | (JP) ................................... 210/690 |

OTHER PUBLICATIONS

Anderson, K. and Ness, P., eds., 1994, *Scientific Basis of Transfusion Medicine: Implications for Clinical Practice*, W.B. Saunders Company, Philadelphia, PA.

Burstein, M. et al., 1957, "Sur la precipitation selective des β lipoproteins du serum par l'heparine et les heparindoides de synthese en presence due $Cl_2Ca$," *Journal de Physiologie (Paris)*, vol. 49, pp. 83–86.

Calhoun, L., 1996, "Chapter 13: Blood Product Preparation and Administration," pp. 305–333 in *Clinical Practice of Transfusion Medicine, Third Edition*, editors L.D. Petz et al., Churchill Livingston, New York.

Celite, 1991, "Functional Fillers for Industrial Applications," publication number FF–396 Nov. 1991, Celite Corporation, Lompoc, California, USA (pp. 1–28).

Cohn et al., 1946, "Preparation and Properties of Serum and Plasma Proteins. IV. A System for the Separation into Fractions of the Protein and Lipoprotein Components of Biological Tissues and Fluids," *J. Am. Chem. Soc.*, 1946, vol. 68, pp. 459–475.

Converse, C.A. et al., 1992, ed., *Lipoprotein Analysis: A Practical Approach*, IRL Press.

Curling, J.M., 1980, editor, *Methods of Plasma Protein Fractionation*, Academic Press.

Dwyer, J.M., 1992, "Manipulating the immune system with immune globulin," *N. Engl. J. Med.* vol. 326, pp. 107–116.

E.C. Rossi, T.L. Simon, G.S. Moss, eds., 1991, *Principles of Transfusion Medicine*, Williams and Wilkins, Baltimore, MD.

Guyton, A.C., 1991, *Textbook of Medical Physiology*: eighth edition. W.B. Saunders Company, Philadelphia, PA.

Handin, R.I, et al., 1995, editors, *Blood Principles and Practice of Hematology*, Lippincott, Philadelphia.

Heide, K. et al., "Chapter 8: Plasma Protein Fractionation," pp. 545–597, in *The Plasma Proteins: Structure, Function and Genetic Control*, editor Putnam, F.W., 1977, Academic Press.

Lennarz, W.J., 1980, editor, *The Biochemistry of Glycoproteins and Proteoglycans*, Plenum Press.

Rosselin et al., 1966, "Separation of Antibody–Bound and Unbound Peptide Hormones Labelled with Iodine–131 By Talcum Powder and Precipitates Silica," *Nature*, vol. 212, No. 5060, pp. 355–357.

Taylor, H.F.W., 1964, editor, *The Chemistry of Cements*, Chapter 5, "The Calcium Silicate Hydrates," pp. 168–232, Academic Press.

Walborg, E.F., 1978, editor, *Glycoproteins and Glycolipids in Disease Processes*, Amer. Chem. Soc.

\* cited by examiner

*Primary Examiner*—Joseph W. Drodge
(74) *Attorney, Agent, or Firm*—Morrison & Foerster LLP

(57) ABSTRACT

The present invention pertains to improved methods for the selective separation of organic components from biological fluids. More particularly, the present invention pertains to methods for the selective separation of organic components from biological fluids which comprise the step of contacting the biological fluid with a synthetic hydrated alkaline earth silicate (i.e., SHAES), such as synthetic hydrated calcium silicate (i.e., SHCS) or synthetic hydrated magnesium silicate (i.e., SHMS). In a preferred embodiment, the present invention pertains to such methods where the biological fluid is a mammalian blood fluid (e.g., whole blood, blood plasma, blood serum, blood fraction, plasma fraction, serum fraction).

32 Claims, No Drawings

METHODS FOR THE SELECTIVE SEPARATION OF ORGANIC COMPONENTS FROM BIOLOGICAL FLUIDS

RELATED APPLICATIONS

This application is a 35 U.S.C. § 371 application based on international application serial number PCT/US96/20034, filed Dec. 20, 1996, which claims priority to U.S. provisional patent application Ser. No. 60/021,545 filed Jul. 10, 1996, the disclosure of which is hereby incorporated by reference.

TECHNICAL FIELD

The present invention pertains to improved methods for the selective separation of organic components from biological fluids. More particularly, the present invention pertains to methods for the selective separation of organic components from biological fluids which comprise the step of contacting the biological fluid with a synthetic hydrated alkaline earth silicate (i.e., SHAES), such as synthetic hydrated calcium silicate (i.e., SHCS) or synthetic hydrated magnesium silicate (i.e., SHMS). In a preferred embodiment, the present invention pertains to such methods where the biological fluid is a mammalian blood fluid (e.g., whole blood, blood plasma, blood serum, blood fraction, plasma fraction, serum fraction).

BACKGROUND

Throughout this application, various publications, patents, and published patent applications are referred to by an identifying citation. Corresponding complete citations are provided below under the heading "References." The disclosures of the publications, patents, and published patent specifications referenced in this application are hereby incorporated by reference into the present disclosure to more fully describe the state of the art to which this invention pertains.

Blood is the fluid that circulates in the blood vessels of the body, that is, the fluid that is circulated through the heart, arteries, veins, and capillaries. The function of the blood and the circulation is to service the needs of other tissues: to transport oxygen and nutrients to the tissues, to transport carbon dioxide and various metabolic waste products away, to conduct hormones from one part of the body to another, and in general to maintain an appropriate environment in all tissue fluids for optimal survival and function of the cells. See, for example, Guyton, 1991.

Blood consists of a liquid component, plasma, and a solid component, cells and formed elements (e.g., erythrocytes, leukocytes, and platelets), suspended within it. Erythrocytes, or red blood cells account for about 99.9% of the cells suspended in human blood. They contain hemoglobin which is involved in the transport of oxygen and carbon dioxide. Leukocytes, or white blood cells, account for about 0.1% of the cells suspended in human blood. They play a role in the body's defense mechanism and repair mechanism, and may be classified as agranular or granular. Agranular leukocytes include monocytes and small, medium and large lymphocytes, with small lymphocytes accounting for about 20–25% of the leukocytes in human blood. T cells and B cells are important examples of lymphocytes. Three classes of granular leukocytes are known, neutrophils, eosinophils, and basophils, with basophils accounting for about 65–75% of the leukocytes in human blood. Platelets (i.e., thrombocytes) are not cells but small spindle-shaped or rodlike bodies about 3 microns in length which occur in large numbers in circulating blood. Platelets play a major role in clot formation.

Plasma is the liquid component of blood. It serves as the primary medium for the transport of materials among cellular, tissue, and organ systems and their various external environments, and it is essential for the maintenance of normal hemostasis. One of the most important functions of many of the major tissue and organ systems is to maintain specific components of plasma within acceptable physiological limits.

Plasma is the residual fluid of blood which remains after removal of suspended cells and formed elements. Serum is the fluid which is obtained after blood has been allowed to clot and the clot removed. Serum and plasma differ primarily in their content of fibrinogen and several components which are removed in the clotting process. Plasma may be effectively prevented from clotting by the addition of an anticoagulant (e.g., sodium citrate, heparin) to permit handling or storage. Plasma constitutes about 4% of total body weight in humans. It is composed primarily of water (approximately 90%), with approximately 7% proteins, 0.9% inorganic salts, and smaller amounts of carbohydrates, lipids, and organic salts. See, for example, Carlson, 1991.

The protein portion of plasma and serum is a mixture of a large number different protein components. Standard methods, such as precipitation by various salts or organic compounds, electrophoresis, ultracentrifugation, ion-exchange chromatography, gel filtration, and immunoprecipitation with antibody-containing antisera, have been variously employed to identify and characterize at least 100 distinct protein components in human plasma. See, for example, Putnam, 1975–1987; Handin et al., 1995. Five major fractions of blood protein (as determined electrophoretically) are albumin, $\alpha 1$-globulin, $\alpha 2$-globulin, $\beta$-globulin, and $\gamma$-globulin.

In human blood, approximately one-half of blood protein is albumin, a relatively small protein with molecular weight of 69,000. Albumin contributes greatly to the colloid osmotic pressure of plasma and thus plays a major role in the regulation of intravascular volume and the fluid exchange between the vascular system and extravascular system. Albumin also serves as a transport protein for various substances, including small ions such as calcium and iodine and organic compounds such as bilirubin.

In human blood, the $\alpha 1$-globulin fraction contains proteins such as $\alpha 1$-acid glycoprotein, $\alpha 1$-antitrypsin, and $\alpha 1$-lipoprotein. The $\alpha 2$-globulin fraction contains proteins such as $\alpha 2$-macroglobulin, haptoglobulin, ceruloplasmin, and group-specific complement. The $\beta$-globulin fraction contains proteins such as transferrin, hemopexin, $\beta 1$-lipoprotein, $\beta 2$-microglobulin, and complement components. The $\gamma$-globulin fraction contains proteins such as immunoglobulins and C-reactive protein.

Immunoglobulins (which are antibodies found circulating in the blood) represent approximately one-sixth of the total human blood protein and largely constitute the $\gamma$-globulin fraction. Of the different classes of immunoglobulins which can be distinguished, the principle ones are IgG, IgM, IgA, IgD, and IgE.

In addition to albumin and immunoglobulins, lipoproteins are another class of blood components and account for approximately 10% of total human blood protein. Lipoproteins are water soluble complexes comprising protein components (e.g., apolipoproteins) and lipid components (e.g., cholesterol, cholesteryl esters, phospholipids, and triglycerides). Lipoproteins are often conveniently considered to comprise a hydrophobic core (primarily of cholesteryl esters and triglycerides) surrounded by a relatively more hydrophilic shell (primarily apolipoproteins, phospholipids, and unesterified cholesterol) projecting its hydrophilic domains into the aqueous environment. Lipoproteins presumably serve as transport proteins for lipids, such as triacylglyercols, cholesterol (and cholesteryl esters), and other lipids (e.g., phospholipids). Lipoprotein remnants are the biological byproducts produced in the metabolism of lipoproteins.

Three classes of lipoproteins, α1-lipoprotein, pre-β-lipoprotein, and β1-lipoprotein, can be distinguished in human blood, according to their electrophoretic behavior. However, lipoproteins are more conveniently characterized by their ultracentrifligation behavior in high-salt media, as described by their flotation constants (densities), as follows: chylomicra, less than 1.006; very low density (VLDL), 1.006–1019; low density (LDL), 1.019–1.063; high density (HDL), 1.063–1.21; very high density (VHDL), >1.21. Lipoproteins are often approximately spherical in shape, and range in diameter from about 0.1 micron (for chylomicra) to about 5 nanometers (for VHDL). Lipoproteins range in molecular weight from 200 kd to 10,000 kd and from 4 to 95% lipid (the higher the density the lower the lipid content). The very low- and low-density fractions appear in the β1-globulin fraction and the high-density and very high-density fractions appear in the α1-globulin fraction. Chylomicra and VLDLs are rich in triglycerides (~90% and ~60% of the total lipid content, respectively), while LDLs are rich in cholesterol (~60% of total lipid content) and HDLs are rich in phospholipids (~50% of total lipid content). See, for example, Converse et al., 1992.

Apolipoproteins are the protein component of lipoproteins. Examples of apolipoproteins which have been isolated from human blood and characterized include apolipoproteins A-1, A-2, A-4, B-48, B-100, C, D, and E.

Triacylglycerols (also known as triglycerides or neutral fats) are electrically neutral esters of glycerol and which possess acyl groups that are often derived from fatty acids. Examples of fatty acids include long-chain fatty acids such as lauric acid, myristic acid, palmitic acid, stearic acid, arachidic acid, behenic acid, lignoceric acid, palmitolic acid, oleic acid, linoleic acid, linolenic acid, and arachidoneic acid. Cholesterol triglyceride is a triglyceride where one or more acyl group is derived from cholesterol. Other glycerol esters include monoacylglycerols and diacylglycerols.

Cholesterol, the most abundant steroid in animal tissues, is usually present in blood as a lipid component of a lipoprotein. Cholesterol is a biological precursor of five major classes of steroid hormones (the progestagens, glucocorticoids, mineralocorticoids, androgens, and estrogens) which are also usually present in blood as a lipid component of a lipoprotein (i.e., they are also associated with a lipoprotein complex). Examples of such steroids include progesterone, cortisol, aldosterone, testosterone, and estrone. Cholesteryl esters, such as the apolipoproteins A1, B, C, and E, are examples of other cholesterol derivatives.

Phospholipids are lipids which comprise phosphorus; often phospholipids also contain nitrogen. Examples of phospholipids include those derived from glycerol (i.e., phosphoglycerides), such as phosphatidyl cholines, phosphatidyl ethanolamines, phosphatidyl serines, phosphatidyl inositols, and phosphatidyl glycerols. Other examples of phospholipids include those derived from sphingosine (i.e., sphingolipids), such as ceramides and sphingomyelins.

Glycolipids, another class of blood components, are lipids which comprise at least one carbohydrate group (e.g., sugar residue). Most glycolipids can be classified as glycosphingolipids (which are derived from sphingosine) or glycoglycerols (which are derived from glycerol). Mammalian glycolipids are usually derived from sphingosine. Many glycolipids may be further classified as neutral-, sulfo-, or phospho-glycosphingolipids or -glycoglycerols. Examples of simple glycosphingolipids include the cerebrosides in which there is only one sugar residue, often glucose, lactose or galactose. Examples of more complex glycosphingolipids include the gangliosides, which possess a branched chain of as many as seven sugar residues, as well as hematosides, globosides, and trihexosylceramide. See, for example, Walborg, 1978.

A number of blood proteins function as carriers for specific substances and are often referred to as transport proteins. These include apolipoproteins, discussed above, which form lipoprotein complexes with lipids, and thus are believed to facilitate the transport of these lipids. Other transport proteins include those which transport metal ions, such as the iron-binding protein, transferrin, and the copper-binding protein, ceruloplasmin, and 9.5 S-α1-glycoprotein. Prealbumin and the thyroxin-binding globulin transport the thyroid hormone, and transcortin transports the steroid hormones. Hemoglobin is eliminated from the circulation by haptoglobin, and heme is bound to hemopexin. The retinol-binding globulin binds vitamin A. The transcobalamins I, II, and III bind vitamin B12. Gc-globulin binds vitamins D2 and D3.

A number of blood proteins are enzymes, pro-enzymes, or enzyme inhibitors. Blood proteins which are enzymes (e.g., proteinases) include, for example, cholinesterase, ceruloplasmin, plasminogen, protein C, and β2-glycoprotein I. Pro-enzymes (i.e., zymogens) are converted to enzymes by the action of specific enzymes. Proteinase inhibitors control this process by reducing or eliminating the activity of these specific enzymes. The major proteinase inhibitor found in human blood is α1-antitrypsin (i.e., α1-proteinase inhibitor; α1-trypsin inhibitor, prolastin) which protects tissues from digestion by elastase. Another class of proteinase inhibitors found in human blood are the antithrombins, such as antithrombin III, which prevent the effects of thrombin. Still another proteinase inhibitor found in human blood is C1-esterase inhibitor, which reduces or eliminates the activity of C1-esterase, which is the activated first component of complement, C1. Other blood proteins which are enzyme inhibitors include α1-antichymotrypsin, inter-α-trypsin inhibitor, α2-macroglobulin, and α2-antiplasmin.

A number of blood proteins are involved with the clotting process (i.e., coagulation factors). Blood clots are formed by an enzymatic cascade, with the activated form of one factor catalyzing the activation of the next factor which results in a large amplification and a rapid response to trauma. Examples of inactivated and activated clotting factors include, for example, XII and XIIa; XI and XIa; IX and IXa; X and Xa; VII and VIIa; II (prothrombin) and Ia (thrombin); I (fibrinogen) and Ia (fibrin). Other clotting factors include kininogen, kallikrein, and factors VIII, VIIIa, V, Va, XIII, and XIIIa. A number of clotting factors are also referred to as vitamin K dependent proteins, including, for example, Factor II (prothrombin), Factor VII, Factor IX, Factor X, Protein C, and Protein S.

A number of blood proteins are complement components and together comprise the complement system, which lyses microorganisms and infected cells by forming holes in their plasma membrane. More than 15 complement proteins are known, including C1, C1q, C1r, C1s, C2, C3, C4, C5, C6, C7, C8 and C9.

Proteins which comprise at least one carbohydrate group (e.g., sugar residue) may be classified as glycoproteins (often also referred to as mucoproteins). The term seromucoid is often used to refer to glycoproteins derived from blood serum. In glycoproteins, typically one or more sugar residues are attached to the protein via the side chain of an amino acid residue. Many blood proteins, and virtually all plasma proteins except albumin, are glycoproteins. For example, γ-globulins (e.g., immunoglobulins), α1-globulins, and α2-globulins, are glycoproteins. Examples of glycoproteins which have been isolated from human blood include α1-acid glycoprotein, α2-glycoprotein, α2-macroglobulin, α2-HS-glycoprotein, α1-antichymotrypsin, α1-antitrypsin, fibrinogen, fibronectin, pre-albumin, hemopexin, haptoglobin, transferrin, ceruloplasmin, many clotting factors, and many components of the complement system. Glycoproteins are found in substances such as orosomucoids (primarily α1-acid glycoprotein), mucin (a cell secretion), and ovomucoids (derived from egg white), which contain high quantities (e.g., about 30–50%) of carbohydrates. See, for example, Lennarz, 1980.

In addition, the liquid fraction of blood also contains a number of other components, such as electrolytes, carbohydrates, lipids, and organic salts. Electrolytes help regulate the osmotic pressure and pH of plasma. The primary cations are sodium, potassium, calcium, and magnesium. The primary anions are chloride, bicarbonate, phosphate, sulfate, and organic acids. The liquid fraction of blood also contains other small molecules (many of which are bound to proteins while transported in the blood), such as sugars (e.g., glucose), free amino acids (e.g., glutamine, alanine, glycine, and lysine), urea, uric acid, creatinine, pyruvic acid, non-esterified fatty acids (i.e., free fatty acids, FFA), bilirubin, vitamins (e.g., vitamin A), steroid hormones, and small peptides (e.g., angiotensin and bradykinin).

Human blood is a source material for the preparation of a number of blood products for clinical use. See, for example, Lawrence et al., 1996. Such blood products include, for example, whole blood (WB), red blood cells (RBC), platelets (PLT), leukocytes, fresh frozen plasma (FFP), plasma, serum, cryoprecipitated antihemophilic factor (CRYO), Factor VIII concentrates, Factor IX concentrates (prothrombin complex), albumin, plasma protein fraction (PPF), immune serum globulin (ISG), and hyperimmunoglobulins (RhD).

Human blood plasma is a valuable source material for the preparation many of these blood products. A number of organizations throughout the world are involved in the fractionation of human plasma into a variety of derivatives intended for clinical use. Among the products licensed for use in the United States are albumin, plasma protein fraction (PPF), immunoglobulin for intravenous or intramuscular injection, antihemophilic factor, Factor IX complex (the vitamin K-dependent factors), coagulation Factor IX, α1-antitrypsin (i.e., α1-proteinase inhibitor), and antithrombin III. Other products available in Europe include fibrin sealant, von Willebrand factor, Factor XIII, and C1-esterase inhibitor. See, for example, Drohan, 1994. Albumin, which is used as a plasma volume expander, is one of the major products of plasma fractionation. PPF is an albumin-rich fraction of plasma of lower purity obtained by a simpler fractionation scheme; it is more economical to produce than albumin and can be recovered in higher yield.

Other blood products include isolated immunoglobulins. Immunoglobulins are prepared from the plasma of unselected normal donors, while hyperimmunoglobulins are prepared from the plasma of donors with high antibody titers against specific antigens (e.g., tetanus, hepatitis B, Rh-D blood group antigen, and rabies). These hyperimmune donors may be identified during convalescent periods after infection or transfusion, or they may be specifically immunized to produce the desired antibodies. The immunoglobulins are usually administered intramuscularly. Intravenous immunoglobulin (IGIV) products have been developed using a variety of methods to remove or inactivate any anticomplementary aggregates. The development of IGIV has permitted the administration of much higher dosages, with a subsequent expansion in immunoglobulin therapy. See, for example, Drohan, 1994, at Chapter 138. Established indications for intravenous immunoglobulin include primary antibody deficiencies (such as congenital agammaglobulinemia, common variable immunodeficiency, X-linked agammaglobulinemia, severe combined immunodeficiency, Wiskott-Aldrich syndrome), idiopathic thrombocytopenic purpura (ITP), and B-cell chronic lymphocyte leukemia (CLL). Other conditions in which clinical benefit has been reported are secondary immunodeficiencies (multiple myeloma, protein-losing enteropathy, nephrotic syndrome), Kawasaki syndrome, treatment of viral diseases (such as human immunodeficiency virus (HIV) and cytomegalovirus infections), burn therapy, and prevention of graft-versus-host disease in bone marrow recipients. See, for example, Dwyer, 1992.

The development of coagulation factor concentrates has resulted in dramatic increases in the life expectancy and the quality of life of patients with hemophilia. Factor VIII and Factor IX concentrates are available for the treatment of hemophilia A and B, respectively. In addition, some Factor VIII concentrates contain appreciable amounts of von Willebrand factor (vWF) and may be used for the treatment of von Willebrand disease, whereas Factor IX complex concentrates can be used for the treatment of other congenital or acquired deficiencies of vitamin K dependent plasma proteins. Other plasma proteins combine to form a fibrin sealant which is used in a variety of surgical situations for its hemostatic and adhesive properties. The first component is derived from human plasma and contains fibrinogen, Factor XIII, fibronectin, and small amounts of plasminogen and other plasma proteins. The second component is a thrombin solution of sufficient concentration to clot the fibrinogen rapidly. See, for example, Drohan, 1994.

The proteinase inhibitors present in human plasma play critical roles in the regulation of the proteolytic cascades of the coagulation, fibrinolytic, complement, and kinin systems. Proteinase inhibitor concentrates have been developed to treat diseases caused by hereditary deficiencies of α1-antitrypsin (i.e., α1-proteinase inhibitor), antithrombin III, and C1-esterase inhibitor. Patients with hereditary deficiencies of α1-antitrypsin inhibitor develop pulmonary emphysema and liver disease. Clinical studies have shown that antithrombin III (AT-III) concentrates are effective in the prophylaxis or treatment of thromboembolic disorders in patients with hereditary AT-III deficiency. C1-esterase inhibitor can be used to treat hereditary angioedema, an autosomal-dominant disease that is characterized by episodic swelling of the subcutaneous tissues and the mucosa of the gastrointestinal and respiratory tracts. See, for example, Drohan, 1994.

The preparation of blood products from blood typically involves a combination of separation steps. For example, in the preparation of blood products derived from plasma, whole blood is typically first processed to removed suspended cells and formed elements (e.g., by centrifugation) to yield blood plasma. Alternatively, blood serum may be obtained by forming a blood clot (e.g., initiated by the addition of thrombin and calcium ion) and subsequently removing the clot (e.g., by centrifugation). The methods described below for the processing of blood plasma are also generally applicable to the processing of blood serum.

In the preparation of blood products and the isolation and characterization of blood components derived from blood plasma, substantial resources are expended in the field of plasma fractionation; that is, in methods for dividing plasma into the fractions rich in particular blood components, and fractions poor in particular blood components. See, for example, Curling, 1980.

Historically, plasma fractionation was achieved by salt precipitation typically using mineral salts such as ammonium sulfate and sodium sulfate; the proteins were precipitated as a result of an increase in salt concentration. In the 1940's, Cohn et al. developed an effective alternative precipitation method which employed an organic solvent, ethanol. For example, in the well known "Cohn's Method 6" (Cohn et al., 1946), ethanol is added to plasma at specific conditions of pH and temperature to obtain a specific ethanol concentration, and the resulting precipitate separated from the supernatant, and the precipitate retained. The supernatant is again treated with ethanol using different specific conditions, and the resulting second precipitate separated from the second supernatant, and the precipitate retained. The process is repeated stepwise, so that the resulting second supernatant is similarly processed, yielding a third precipitate and a third supernatant, and so on, thus yielding a sequence of precipitates (e.g., Cohn Precipitates I, II+III, IV-1, IV-4, and V; Cohn Supernatants I, II+III, IV-1, IV-4, and V), each rich in particular plasma components.

A number of other methods of fractionation by precipitation have been developed, including, for example, the use other precipitation agents such as ammonium sulfate, Rivanolg, caprylic acid, ether, and polyethylene glycol. Cryoprecipitation (e.g., the formation of a precipitate from a solution by cooling) has also been used to prepare blood fractions, most importantly a plasma cryoprecipitate rich in Factor VIII. In recent years, chromatographic methods (e.g., ion exchange chromatography, affinity chromatography, and gel filtration) have been developed to effect fractionation. In many cases, two or more fractionation methods are employed stepwise to effect the desired fractionation.

Liquid-solid separations are critical in virtually all plasma fractionation procedures in order to harvest desired components and remove contaminants. Filtration and centrifugation are two methods typically used to effect liquid-solid separations. In many instances both methods are used, stepwise, to achieve the desired separation.

Many plasma processing procedures employ filtration through relatively coarse filter media to clarify the liquid (e.g., prefiltering), often using a depth filtration process. For example, plasma may be filtered through asbestos sheet filters, often in combination with diatomaceous earth as a filter precoat. A variety of such filters are commercially available (e.g., from Seitz®, Ertel®, Alsop®, Cellulo®). More recently, plasma has been clarified using alternative cationic depth filters comprising cellulose and diatomaceous earth treated with a cationic charge modifier. A variety of such filters are commercially available (e.g., from AMF Cuno®). Other (e.g., anionic) materials suitable for clarification are also known and commercially available (e.g., from Millipore® and Pall®).

Many plasma processing procedures also employ filtration through relatively fine filtration media. Such fine filtration media include membrane filters having pore diameters of about 0.1 to 10 microns. A variety of such filters are commercially available (e.g., from Millipore®, Gelman Sciences®, Nuclepore®, Pall®, Sartorius®&). For example, sterile filtration typically involves passage of the liquid through one or more membrane filters having pore diameters of about 0.2 microns or less, in order to exclude microorganisms, such as Pseudomonas bacteria.

Since most plasma processing procedures employ at least one precipitation or chromatographic fractionation step, these procedures invariably include further steps to eliminate the precipitating or eluting agents and to concentrate the final product. Methods for achieving one or both of these goals include lyophilization, thin film evaporation, gel permeation, and ultrafiltration. Thin film evaporation methods are typically used to remove organic solvents. Gel permeation methods are typically used to remove precipitating agents, such as ethanol and salts, but yield the desired product in a dilute solution.

Ultrafiltration (i.e., nanofiltration, dialysis) is often performed to achieve one or both goals. In many cases, gel permeation in combination with ultrafiltration is employed to obtain the desired product purity and concentration. Ultrafiltration methods employ ultrafine filtration media, including, for example, flat membranes, spiral membranes, hollow fiber systems, and tubular systems. A variety of such filter materials are commercially available (e.g., from A/G Technology®, Millipore®). Common ultrafiltration membranes are comprised of hollow fiber filters or flat sheet filters (e.g., comprising polyvinylidene fluoride, polysulfone, and/or cellulose ester) having an effective size exclusion of about 25–500 nanometers, or about 1,000 to 500,000 kd.

Filtration (e.g., of plasma, plasma fractions, or partially purified blood products) through fine and/or ultrafine filtration media is invariably hampered by rapid clogging (e.g., fouling) of the filtration media resulting in a low, often impractical, flow rate through the media, as well as increased costs. For example, if plasma protein fraction (i.e., PPF) is filtered directly through a 0.2 micron or tighter membrane filter, the throughput is very low and a large amount of the membrane is required to filter even relatively small amounts of PPF. Blood components (e.g., lipids, lipid complexes, lipid-like materials, colloids) often cause filtration and separation problems, such as fouling, clogging or otherwise impairing (e.g., "blinding off") filtration and separation media, such as ultrafiltration media and/or chromatographic media. However, it has been found that the materials which cause clogging can often be removed by a pre-filtration step through relatively coarse filtration media (as described above), thereby permitting a high throughput through fine and/or ultrafine filtration media, and thus increasing efficiency and reducing costs.

Although pre-filtration methods have increased the efficiencies of fine filtration and ultrafiltration, other methods have been examined. For example, pre-treatment methods for the removal of materials (e.g., lipids, lipid complexes, lipid-like materials, colloids) which cause clogging of the filtration media have been investigated.

For example, a common pre-treatment method involves the use of colloidal fumed silica at a rate of about 40 grams per liter of liquid being treated (i.e., ~0.04 g/mL) (Condie, 1979). Lipoproteins, cholesterol, and triglycerides are adsorbed on the colloidal fumed silica, and the resulting residue is removed by centrifugation. Unfortunately, a large proportion of the liquid (20–50% of the starting volume) remains trapped within the centrifuged precipitate. This trapped volume often contains significant quantities of the product sought, and is difficult to recover. Additionally, the colloidal fumed silica is not very selective, and significant amounts of albumin and serum immunoglobulins are removed along with the lipids.

Another pre-treatment method involves the use of tricalcium phosphate (i.e., $Ca_3(PO_4)_2$) at a rate of about 20–50 grams per liter of liquid being treated (i.e., ~0.02–0.05 g/mL) (Burstein et al., 1957). It is believed that the interaction between many lipids (e.g., chylomicra and β1-lipoproteins) and calcium results in precipitation. The resulting colloidal slurry is then centrifuged to remove the tricalcium phosphate and bound lipids.

Yet another pre-treatment method involves the precipitation of lipoproteins from plasma by the addition of dextran sulfate (i.e., a heparin-like polysaccharide containing up to three sulfate groups per sugar residue) at a rate of about 0.1–0.5% w/v (i.e., 0.001–0.005 g/mL). The resulting lipid-rich precipitate is then removed by centrifugation. However, the clarified serum or plasma then contains dextran sulfate, and additional processing is required for its removal.

The present invention provides methods for the selective separation of organic components (e.g., lipids, lipid complexes, lipid-like materials, colloids, and components thereof) from biological fluids containing them, which methods comprise the step of contacting the biological fluid with a synthetic hydrated alkaline earth silicate (i.e., SHAES), such as synthetic hydrated calcium silicate (i.e., SHCS) or synthetic hydrated magnesium silicate (i.e., SHMS). In one embodiment, the methods of the present invention are useful as pre-treatment methods in the preparation of blood products and in the isolation and characterization of blood components derived from blood.

Synthetic hydrated alkali earth silicates have been described in methods for the processing of certain liquids. For example, hydrated calcium silicate has been described in methods for the removal of colloids and color forming materials in the purification of sugar solutions (Bottoms, 1951). Hydrated calcium silicates have also been described as a sweetener for organic dry cleaning solvents to remove free fatty acids (i.e., FFA) which accumulate upon repeated usage (Riede, 1963). Compositions comprising diatomaceous earth, synthetic calcium silicate hydrate, and synthetic magnesium silicate hydrate have been described in methods for the reduction of the free fatty acid (i.e., FFA) content and color degradation in cooking oils used in fast food outlets and other restaurants (see, for example, Duensing et al., 1978). Synthetic hydrated calcium silicates have been described as drying agents in methods for drying delactosed or deproteinized solutions obtained as by-products in the concentration of whey proteins and casein (Lauck et al., 1983). Base-treated magnesium silicates have been described as adsorbents in methods for the removal of contaminants such as free fatty acids (i.e., FFA), soaps, phosphorus, metal ions, and color bodies from glyceride oil (Denton, 1993). Synthetic hydrated alkaline earth silicates have been described as absorbents (e.g., for converting liquids or low melting point solids to free flowing powders) and as fillers, carriers, flatting agents, decolorizers, and catalyst carriers (Celite, 1991).

The present disclosure represents the first use of synthetic hydrated alkaline earth silicate (i.e., SHAES) in methods for the preparation, isolation, and/or characterization of biological products for clinical use, and in particular, for organic components of mammalian blood.

SUMMARY OF THE INVENTION

One aspect of the present invention pertains to methods for the selective separation of an organic component from a biological fluid comprising said organic component, said methods comprising the step of contacting said biological fluid with a synthetic hydrated alkaline earth silicate. A preferred embodiment of the present invention pertains to methods for the selective separation of an organic component from a biological fluid comprising said organic component, said methods comprising the steps of (a) contacting said biological fluid with a synthetic hydrated alkaline earth silicate, thereby forming (i) a residue comprising said synthetic hydrated alkaline earth silicate residue and said organic component, and (ii) remaining fluid; and (b) separating said residue from said remaining fluid. In some preferred embodiments, said biological fluid is selected from the group consisting of bodily fluids, cell culture fluids, cell lysate fluids, and culture media fluids, more preferably bodily fluids, still more preferably mammalian blood fluids, yet more preferably mammalian blood plasma fluids. In some preferred embodiments, said organic component is a mammalian blood component. In still other preferred embodiments said organic mammalian blood component comprises lipoprotein, triacylglycerol, cholesterol or a cholesteryl ester, phospholipid, glycolipid, or glycoprotein.

Another aspect of the present invention pertains to methods for the selective separation of an organic component from a biological fluid comprising said organic component and a second organic component, said methods comprising the steps of (a) contacting said biological fluid with a synthetic hydrated alkaline earth silicate, thereby forming (i) a residue comprising said synthetic hydrated alkaline earth silicate residue and said organic component, and (ii) remaining fluid comprising said second organic component; and (b) separating said residue from said remaining fluid. In some preferred embodiments, said biological fluid is selected from the group consisting of bodily fluids, cell culture fluids, cell lysate fluids, and culture media fluids, more preferably bodily fluids, still more preferably mammalian blood fluids, yet more preferably mammalian blood plasma fluids. In some preferred embodiments, said organic component is a mammalian blood component and said second organic mammalian blood component is a mammalian blood protein, more preferably α1-proteinase inhibitor.

Still another aspect of the present invention pertains to methods for the selective separation of an organic component from a biological fluid comprising said organic component, said methods comprising the steps of (a) contacting said biological fluid with a synthetic hydrated alkaline earth silicate, thereby forming (i) a residue comprising said synthetic hydrated alkaline earth silicate residue and said organic component, and (ii) remaining fluid; (b) separating said residue from said remaining fluid; and (c) eluting said organic component from said residue. In some preferred embodiments, said biological fluid is selected from the group consisting of bodily fluids, cell culture fluids, cell lysate fluids, and culture media fluids, more preferably bodily fluids, still more preferably mammalian blood fluids, yet more preferably mammalian blood plasma fluids. In some preferred embodiments, said organic component is a mammalian blood component, more preferably an apolipoprotein or a coagulation factor, more preferably coagulation Factor IX.

In some preferred embodiments, said synthetic hydrated alkaline earth silicate comprises synthetic hydrated calcium silicate. In a more preferred embodiment, said synthetic hydrated alkaline earth silicate comprises synthetic hydrated calcium silicate, and the ratio of said synthetic hydrated calcium silicate to said biological fluid is 0.001 to 0.05 g/mL.

As will become apparent, many preferred features and characteristics of one aspect of the invention are applicable to other aspects of the invention.

DESCRIPTION OF THE PREFERRED EMBODIMENTS

The present invention provides methods for the selective separation of organic components from biological fluids containing them, which methods comprise the step of contacting the biological fluid with a synthetic hydrated alkaline earth silicate (i.e., SHAES), such as synthetic hydrated calcium silicate (i.e., SHCS) or synthetic hydrated magnesium silicate (i.e., SHMS).

It may be convenient to consider the SHAES as acting as a selective capture agent for organic components. Without being bound to any particular theory, the inventors theorize that the alkali earth metal atoms (e.g., calcium, magnesium) of the SHAES act as a selective attractant for organic components and thereby cause them to become adsorbed. The physical structure of the SHAES (e.g., surface area, porosity, pore size, pore volume) may also further result in a sieving of colloidal complexes, thereby assisting the selective capture of the organic components of such complexes. While the SHAES is often a particularly effective capture agent for many organic components (e.g., lipids, lipid complexes, lipid-like materials, and colloidal materials), it is often a particularly ineffective capture agent for other organic components (e.g., albumin). In this way, the capture properties of SHAES provide a basis for the selective separation of organic components.

In one embodiment, the SHAES, acting as a capture agent, permits the selective separation of contaminating organic components from biological fluids, thus permitting more efficient processing of the remaining biological fluid to obtain a desired organic component.

For example, many biological fluids which contain desired organic components also contain contaminating organic components which inhibit or otherwise complicate further processing (e.g., filtration, clarification, purification) often by fouling the media. The methods of the present invention permit the easy removal (e.g., partial or complete) of such contaminating organic components, thereby permitting more efficient processing.

In this regard, the present invention also provides methods for the purification of a desired organic component from a biological fluid which also comprises at least one contaminating organic component, which method comprises the steps of contacting the biological fluid with a SHAES to form a residue (which comprises the SHAES and the contaminating organic component), and separating the residue from the remaining fluid (which comprises the desired organic component).

In another embodiment, the SHAES, acting as a capture agent, may permit the selective separation of a desired organic component, and thus permit the purification (e.g., and/or isolation) of the desired organic component.

For example, many methods for the purification of desired organic components from biological fluids containing them are often intensive, expensive, time consuming, and frequently suffer from low yield. The methods of the present invention permit the harvesting of the desired organic component (by capturing it with SHAES), thereby permitting more efficient purification, isolation, and/or characterization.

In this regard, the present invention also provides methods for the separation (e.g., purification and/or isolation) of a desired organic component from a biological fluid, which method comprises the steps of contacting the biological fluid with a SHAES to form a residue (which comprises the SHAES and the desired organic component), separating the residue from the remaining fluid, and eluting the desired organic component from the residue.

As the SHAES appears to be particularly effective for the capture of lipids (i.e., lipids, lipid complexes, lipid-like materials, and lipid components thereof), as well as colloidal materials, the methods of the present invention are particularly effective for the separation of such materials from biological fluids. Thus, in one embodiment, the methods of the present invention are particularly effective for removal of such materials to permit more efficient processing of the remaining fluid. In another embodiment, the methods of the present invention are particularly effective for the harvesting of such materials and thus permit their more efficient purification, isolation, and/or characterization. In many cases, such materials further comprise other associated biological components (e.g., as an additional component of a lipid complex) which may be simultaneously harvested.

The term "biological fluid" is used herein to refer to aqueous fluids of biological origin which comprise at least one organic component, including solutions, suspensions, dispersions, and gels, and thus may or may not contain undissolved particulate matter. Preferred biological fluids comprise at least one protein component.

An example of one group of biological fluids are bodily fluids, such as blood (including blood plasma and blood serum), lymph, cerebrospinal fluid, lactation products (e.g., milk), amniotic fluids, urine, saliva, perspiration, tears, including fractions thereof. In a preferred embodiment, the bodily fluids are of mammalian origin, more preferably of human origin.

Another example of a group of biological fluids are cell culture fluids, including those obtained by culturing or fermentation, for example, of single- or multi-cell organisms, including prokaryotes (e.g., bacteria) and eukaryotes (e.g., animal cells, plant cells, yeasts, fungi), and including fractions thereof.

Yet another example of a group of biological fluids are cell lysate fluids including fractions thereof. For example, cells (such as red blood cells, white blood cells, cultured cells) may be harvested and lysed to obtain a cell lysate (e.g., a biological fluid), from which organic components (e.g., hemoglobin, α-interferon, T-cell growth factor, interleukins) may be separated with the aid of the present invention.

Still another example of a group of biological fluids are culture media fluids including fractions thereof. For example, culture media comprising biological products (e.g., proteins secreted by cells cultured therein) may be collected and organic components separated therefrom with the aid of the present invention.

A preferred group of biological fluids are mammalian blood fluids. The term "mammalian blood fluid" is used herein to refer to an aqueous fluid which comprises at least one organic mammalian blood component. Preferred mammalian blood fluids comprise at least one mammalian blood protein. A preferred group of mammalian blood fluids are mammalian blood fractions. Examples of mammalian blood fluids include whole blood, blood plasma, blood serum, blood fractions, plasma fractions, and serum fractions. A more preferred group of mammalian blood fluids are mammalian blood plasma fluids. The term "mammalian blood plasma fluid" is used herein to refer to an aqueous fluid which comprises at least one mammalian blood plasma component. Preferred mammalian blood plasma fluids comprise at least one mammalian blood protein. A preferred group of mammalian blood plasma fluids are mammalian blood plasma fractions.

Examples of mammalian blood fluids include fluids comprising whole blood (WB), red blood cells (RBC), platelets (PLT), leukocytes, and blood substitutes (e.g., fluids which resemble blood and which comprise several blood components pooled from different sources). Examples of mammalian blood plasma fluids include fluids comprising fresh frozen plasma (FFP), plasma, serum, cryoprecipitated antihemophilic factor (CRYO), Factor VIII, Factor IX (prothrombin complex), Factor XIII, albumin, plasma protein fraction (PPF), immune serum globulin (ISG), immunoglobulins, hyperimmunoglobulins, antihemophilic factor, α1-antitrypsin (i.e., α1-proteinase inhibitor), antithrombin III, C1-esterase inhibitor, fibrin sealant, von Willebrand factor, and plasma substitutes (e.g., fluids which resemble plasma and which comprise several blood components pooled from different sources).

The term "organic component" is used herein in the conventional sense to refer to materials which comprise carbon and hydrogen. Preferred organic components are produced by biological processes.

The term "organic mammalian blood component" is used herein in the conventional sense to refer to an organic component which may be found in mammalian blood. While many organic mammalian blood components are found exclusively in mammalian blood, many other organic mammalian blood components may be also found in other materials (e.g., other fluids, tissues, or cells). Various organic mammalian blood components are described in detail above. Examples of preferred organic mammalian blood components include mammalian blood proteins and mammalian blood lipids.

The term "mammalian blood protein" is used herein to refer to a protein which may be found in mammalian blood. Various mammalian blood proteins are described in detail above, and include, for example, albumin, immunoglobulins, transport proteins, enzymes, proenzymes, enzyme inhibitors, coagulation factors, glycoproteins, and apolipoproteins.

The term "mammalian blood lipid" is used herein to refer to a lipid, a lipid complex, a lipid-like material, or a lipid component thereof, which may be found in mammalian blood. Various mammalian blood lipids are described in detail above. Examples of mammalian blood lipids include lipoproteins, which are lipid complexes comprising a apolipoprotein component and a lipid component, as described above. Other examples of mammalian blood lipids include the components of lipoproteins (e.g., triacylglycerols, cholesterol and cholesteryl esters, and phospholipids) and glycolipids. Many lipid complexes often further comprise one or more other organic components which are also associated with the complex. The group of mammalian blood proteins and mammalian blood lipids are not mutually exclusive. For example, a component may be a protein yet be a lipid-like material, as in the case of many glycoproteins.

The term "synthetic hydrated alkaline earth silicate" (i.e., SHAES) is used herein to refer to the class of synthetic silicates which comprise, in chemical combination, silicon (i.e., Si, typically reported as silica, $SiO_2$); an alkaline earth element (i.e., M, typically reported as alkaline earth oxide, MO), such as calcium (i.e., Ca, typically reported as calcium oxide (lime), CaO) or magnesium (i.e., Mg, typically reported as magnesium oxide, MgO), and water (i.e., $H_2O$). Examples of SHAESs include synthetic hydrated calcium silicate (i.e., SHCS) and synthetic hydrated magnesium silicate (i.e., SHMS). In some preferred embodiments, the SHAES is in a particulate, powder, granular or pellet form. In a preferred embodiment, the SHAES is SHCS.

Many methods for the preparation of some SHAES have been described. See for example, Taylor, 1964. SHAES is typically prepared by hydrothermal reaction of a siliceous material (e.g., diatomaceous silica), hydrated alkaline earth oxide, and water. Using these methods, the SHAES possesses a highly desirable intricate and porous microstructure (Celite, 1991).

In many preferred embodiments, the SHAES is SHCS and comprises 45–95% silicon by weight (reported as $SiO_2$), 5–35% calcium by weight (reported as CaO), and 1–20% $H_2O$ by weight. In some preferred embodiments, the SHAES is SHCS and comprises 45–55% silicon by weight (reported as $SiO_2$), 25–35% calcium by weight (reported as CaO), 1–20% $H_2O$ by weight. Typically, the balance, usually 1–10% by weight, comprises impurities, such as, for example, aluminum (i.e., Al, typically reported as alumina, $Al_2O_3$), alkali metals (e.g., sodium, Na, and potassium, K, typically reported as the oxides, $Na_2O$ and $K_2O$, respectively), iron (i.e., Fe, typically reported as $Fe_2O_3$), and magnesium (i.e., Mg, typically reported as the oxide, magnesia, MgO). In many preferred embodiments, the SHAES contains a relatively small amount of soluble aluminum.

In many preferred embodiments, the SHAES is SHCS in powder form, with a particle size of from about 0.01 micron to about 0.10 micron as determined, for example, by x-ray measurements and/or electron microscopy. Of these small particles, aggregates as large as about 100 microns may also be present. In preferred embodiments, the retention on a 325 mesh sieve is less than about 10% by weight, more preferably less than about 8% by weight. In many preferred embodiments, the SHAES is SHCS in powder form with a surface area (as determined, for example, using the B.E.T. method) of more than about 75 $m^2/g$, usually from about 75 to 200 $m^2/g$.

A preferred SHAES, as used in the Examples provided below, is SHCS in a fine powder form which has been prepared by hydrothermal reaction of diatomaceous silica, hydrated calcium oxide (i.e., calcium hydroxide), and water, and which results in the following chemical and physical characteristics: a chemical composition of about 47% silicon by weight (reported as $SiO_2$); about 32% calcium by weight (reported as CaO); about 2.5% aluminum by weight (reported as $Al_2O_3$); about 1.2% sodium and potassium (combined) by weight (reported as $Na_2O$ and $K_2O$); about 0.7% iron by weight (reported as $Fe_2O_3$); about 0.6% magnesium by weight (reported as MgO); with the remainder as water (i.e., $H_2O$); a retention on a 325 mesh sieve of about 6% by weight; and a surface area (as determined using the B.E.T. method) of about 120 $m^2/g$. This preferred SHAES is available from Advanced Minerals Corporation, Lompoc, Calif., USA.

In the methods of the present invention, the biological fluid is contacted with a SHAES. The term "contacted" is used herein in the conventional sense to refer to the step of bringing the biological fluid to be treated into contact with the SHAES. In some embodiments, the biological fluid to be treated may be contacted with the SHAES by mixing the biological fluid and the SHAES. The term "mixing" is used herein in the conventional sense and includes conventional methods for mixing, such as, for example, blending, stirring, shaking, and the like, as may be carried out with the aid of any mechanical means, including, for example, paddles, propellers, blades, shakers, rollers, and the like. In some embodiments wherein the biological fluid to be treated is mixed with the SHAES, it is preferable to maintain the SHAES as a suspension in the biological fluid during the contacting step. In some embodiments, the biological fluid to be treated may be contacted with the SHAES by passing the biological fluid through the SHAES supported on a septum. In such embodiments, the biological fluid may be passed through a bed of the SHAES or through a filter pad, cartridge, or sheet comprising the SHAES.

The ratio of SHAES to biological fluid used in the contacting step may be chosen according the amount of organic component to be captured which is present in the biological fluid, and the degree to which the organic component is to be captured. Increasing the ratio of SHAES to biological fluid will increase the degree to which the organic component is captured. Typically, the ratio of SHAES to biological fluid is from about 0.001 to about 0.1 g/mL. In a preferred embodiment, the ratio of SHAES to biological fluid is from about 0.001 to about 0.05 g/mL. In another preferred embodiment, the ratio of SHAES to biological fluid is about 0.001 to about 0.02 g/mL.

The length of time that the biological fluid to be treated is contacted with the SHAES may be chosen according to the amount of organic component to be captured which is present in the biological fluid, and the degree to which the organic component is to be captured. Increasing the contact time generally increases the degree to which the organic component is captured. In a preferred embodiment, the biological fluid to be treated is contacted with the SHAES for a time of more than about 30 seconds (usually in the range of from about 30 seconds to about 24 hours); more preferably from about 1 minute to about 6 hours; still more preferably from about 10 minutes to 1 hour. In embodiments where the biological fluid to be treated is passed through the SHAES (e.g., on a septum, in a filter sheet, pad, or cartridge), it may be necessary to increase the contact time to permit sufficient capture of the organic component. In a preferred embodiment, the flow rate of the biological fluid to be treated through the SHAES is from about 0.1 to 1.0 mL per minute per 15 $cm^2$.

The temperature at which the biological fluid to be treated is contacted with the SHAES may be chosen according to the physical and chemical properties of the biological fluid and the materials therein. In a preferred embodiment, the biological fluid to be treated is contacted with the SHAES at a temperature of from about $-10°$ C. to about $40°$ C. In another preferred embodiment, the biological fluid to be treated is contacted with the filtration media at room temperature (e.g., about $20°$ C.). The pressure at which the biological fluid to be treated is contacted with the SHAES may range from a moderate vacuum to several atmospheres, but it usually about 1 atmosphere.

The methods of the present invention include the step of contacting a biological fluid with a SHAES, thereby forming a SHAES residue and remaining fluid. In embodiments where the biological fluid to be treated is mixed with the SHAES, it may be desirable, and is often necessary, to subsequently remove or otherwise separate the SHAES residue from the remaining fluid (i.e., treated biological fluid). The SHAES residue may be separated from the treated biological fluid using known methods, including, for example, filtration (e.g., gravity filtration, pressure filtration), sedimentation, centrifugation, and the like. As used herein, the terms "treated biological fluid" and "remaining fluid" refer to the biological fluid which is obtained at some time after contacting of the biological fluid with the SHAES has begun.

Following treatment, it may be desirable to adjust the pH of the treated biological fluid, since contact with the SHAES often results in an increase in pH. The pH of the treated biological fluid may be adjusted to a desired pH using known methods. For example, the pH of the treated biological fluid may be reduced by the addition of a suitable acid (e.g., one which does not denature the desired products) including, for example, acetic acid (i.e., $CH_3COOH$), hydrochloric acid (i.e., HCl), and phosphoric acid (i.e., $H_3PO_4$), typically at concentrations of about 0.1 to 1 N.

In those embodiments where a desired organic component has been captured by the SHAES, it may be desirable to elute (or otherwise release) the desired organic component from the SHAES residue. Methods for eluting organic components (e.g., lipids, proteins), are well known and include, for example, treatment with chelating agents (e.g., citrate) and organic solvents (e.g., ethanol, ether).

The methods of the present invention are particularly useful in the fractionation of mammalian blood. For example, fractionation methods which employ ultrafiltration may greatly benefit from pre-treatment of the fluid to be ultrafiltered according to the methods of the present invention, so as to remove materials (e.g., lipids, lipid complexes, lipid-like materials, colloids) which may cause clogging of the ultrafiltration media. In this way, ultrafiltration efficiency may be greatly improved.

The methods of the present invention are also particularly useful in the preparation of mammalian blood concentrates. For example, a desired blood component may be captured, and subsequently eluted, using the methods of the present invention. In this way, blood components may be purified, isolated, and/or characterized.

Many other modifications and variations of the invention as hereinbefore set forth can be made without departing from the spirit and scope thereof and therefore only such limitations should be imposed as are indicated by the appended claims.

EXAMPLES

Several of the methods of the present invention are described in the following examples, which are offered by way of illustration and not by way of limitation.

Example 1

Treatment of Human Plasma

This example demonstrates how the pre-treatment of human plasma with SHAES effects a removal (e.g., partial or complete) of several blood components.

A sample of human plasma containing adenine dextrose citrate (ADC) anti-coagulant was fractionated by Cohn Method #6 as follows. The plasma was first chilled to $0°$ C. in a jacketed vessel. The chilled plasma was then stirred continuously as ethanol (grade 3A, 95%, $-20°$ C.) was added slowly over a period of one hour to obtain a final concentration of 8% ethanol (v/v) with a suspension temperature of $-2°$ C. The precipitate formed in the Fraction I suspension (comprising primarily fibrinogen) was removed by centrifugation using a Beckman® J6B swinging one liter bucket rotor at 3000 rpm for 10 min at $-2°$ C.

Synthetic hydrated calcium silicate (obtained from Advanced Minerals Corporation, Lompoc, Calif., USA) was added in varying amounts (i.e., 0.01, 0.02, 0.03, and 0.04 g/mL) to the clarified Fraction I supernatant. The slurry was mixed for approximately 30 min at 0° C. The residue was removed by centrifugation (i.e., in a Beckman® J6B swinging one liter bucket rotor at 3000 rpm for 5 min at 0° C.), or by pressure filtering (i.e., through a coarse cellulose Cuno® CPX-01A depth filter pad, at 0° C. with a pressure of 5 psi, 35 kPa).

The concentrations of a number of plasma components in the untreated and treated samples were determined by radial immunodiffusion (i.e., RID) using commercially available kits (Binding Site Ltd©, Birmingham, England). Briefly, RID is an analytical technique based on antibody-antigen reactions. The specific antibody for the target protein is provided in a stationary phase of agarose. The target protein (i.e., the antigen) and control standards are loaded into wells in fixed amounts. The target protein diffuses from the well and, in about three days, a precipitation ring is formed. The ring is the result of the antibody-antigen reaction and the measured diameter is used to determine the concentration of the target protein in the original sample. The amount of plasma component removed by treatment with SHAES was calculated as the difference between the amount observed in control experiments (without treatment) and the amount observed following treatment. The results are summarized in Table 1. In many cases, treatment with as little as 0.01 g/mL SHCS yielded a substantial reduction in the concentration of the plasma components investigated.

TABLE 1

| Plasma Component | SHCS (g/mL) | Amount of Plasma Component Remaining (μg/mL) | Calculated Amount of Plasma Component Removed (μg/mL) |
|---|---|---|---|
| Apo Lipoprotein A | 0 | 418 | — |
|  | 0.01 | 378.8 | 39.2 |
|  | 0.02 | 277.4 | 140.6 |
|  | 0.04 | <228 | > =190 |
| Apo Lipoprotein B | 0 | 350 | — |
|  | 0.01 | 310.8 | 39.2 |
|  | 0.02 | <211 | > =139 |
| α1-Glycoprotein | 0 | 310 | — |
|  | 0.04 | 190.2 | 119.8 |
| α2-Glycoprotein | 0 | 380 | — |
|  | 0.01 | 281.8 | 98.2 |
|  | 0.02 | 85.4 | 294.6 |
| α2-HS-Glycoprotein | 0 | 411 | — |
|  | 0.01 | 353.5 | 57.5 |
|  | 0.02 | 324.7 | 86.3 |
|  | 0.04 | 167.0 | 244 |
| β2-Glycoprotein | 0 | 225 | — |
|  | 0.01 | 132 | 93 |
|  | 0.02 | <85 | > =140 |

Example 2
Improved Ultrafiltration

This example demonstrates how pretreatment of a blood plasma fraction with SHAES permits faster and more efficient ultrafiltration. More specifically, this example demonstrates how pre-treatment effects removal (e.g., partial or complete) of a number of blood components from chromatographically purified α1-proteinase inhibitor (α1-PI) solutions and thus permits faster and more efficient ultrafiltration.

A sample of α1-proteinase inhibitor was chromatographically purified by ion exchange chromatography using a series of columns and exploiting isoelectric points for specific contaminants, as follows. Cohn Fraction IV-1 centrifuged precipitate, obtained using standard methods, was solubilized in an aqueous sodium citrate solution (pH 6.0–7.2) at a ratio of 1:30 precipitate to solution (w/v). Many contaminants were then removed by passing the solution through a DEAE® ion exchange resin and CM Sepharose® ion exchange resin, in that order, and collecting the resulting column filtrate (i.e., the "fall-through" solution).

The fall-through solution containing the α1-proteinase inhibitor was analyzed by standard SDS gel electrophoresis methods (i.e., using a sodium dodecyl sulfate polyacrylamide gel), and found to contain contaminants such as orosomucoids, α2-macroglobulin, α1-acid glycoprotein, apolipoprotein A1, apolipoprotein B, and β2-microglobulin. The electrophoresis results are summarized in Table 2.

In control runs, the fall-through solution (i.e., untreated solution) was further processed without pre-treatment with SHAES. In pre-treatment runs, the fall-through solution was pre-treated with synthetic hydrated calcium silicate (obtained from Advanced Minerals Corporation, Lompoc, California, USA) as follows. Hydrated calcium silicate was added to the fall-through solution (i.e., 100 grams per 50 liters; that is, 0.002 g/mL) at pH 6.4. The slurry was mixed for approximately 30–60 min at 18–22° C. The suspension was then filter clarified by passing through a 293 mm diameter Cellulo® 2350P disk filter pad. The pre-reated solution was also analyzed by standard SDS gel electrophoresis methods and the results are summarized in Table 2. The pre-treated solution retained the desired α1-proteinase inhibitor (the presence of citrate prevents the α1-proteinase inhibitor from being captured by the SHAES); however, many of the contaminants were not detected.

TABLE 2

| Material | Untreated Solution | Treated Solution |
|---|---|---|
| α1-proteinase inhibitor | 45–58.8 kd | 45–58.8 kd |
| HDL lipoprotein | 210 kd | no band |
| α1-acid glycoprotein | 41 kd | no band |
| apolipoprotein A1 | 27 kd | no band |
| apolipoprotein B | 21.5 kd | no band |
| β-2 microglobulin | 15.5 kd | no band |

Samples of the untreated and pre-treated solutions were then identically processed. Prior to ultrafiltration, samples were further clarified by passing through a 0.2 micron Durapore® filter (from Millipore®). Ultrafiltration was effected by passing the solution through a 500K hollow fiber filter (from A/G Technology®) having an area of 7 ft$^2$ (i.e., 0.65 m$^2$) using a back pressure of 15 psi (i.e., 104 kPa), and the permeate collected. During ultrafiltration, the solution being filtered was recirculated at 8–10 liters/hour and maintained at 20° C. The volume of liquid being ultrafiltered (i.e., initial volume) and the final volume of permeate obtained (i.e., permeate volume) were recorded. The rate of accumulation of permeate was also periodically recorded. Ultrafiltration was continued until most of the initial volume (e.g., about 90%) was recovered or until the rate of accumulation of permeate had decreased to about 10–25% of the initial rate (e.g., reached a plugging condition). The results are summarized in Table 3.

TABLE 3

| Run | Initial Volume (liters) | Permeate Volume (liters) | Initial Rate of Accumulation of Permeate (mL/min) | Initial Rate of Accumulation of Permeate (mL/min) |
|---|---|---|---|---|
| Control | 55 | 20 | 1200 | 300 |
| Control | 64 | 40 | 1300 | 180 |
| Pre-treatment | 59 | 55 | 1300 | 800 |
| Pre-treatment | 62 | 58 | 1280 | 658 |

In control runs, the rate of accumulation of permeate decreased steadily and ultrafiltration was discontinued when the rate of accumulation of permeate had decreased to 10–25% of the initial rate and had reached a plugging condition (usually after about 25 to 60 minutes). In contrast, in pre-treatment runs, the rate of accumulation of permeate was only moderately reduced and ultrafiltation was continued to completion. Even at completion, the rate of accumulation of permeate had only been reduced by about 40–50% in pre-treatment runs. The recovery rate (i.e., ratio of permeate volume to initial volume) in pre-treatment runs was substantially higher than in control runs (e.g., about 93% as opposed to 30–65%).

Example 3
Removal of Cholesterol from Human Blood Serum

This example demonstrates how the cholesterol content of blood serum can be reduced by treatment with SHAES.

Three samples of human blood serum (Sigma Chemical Company®) were treated identically. To each 100 mL sample was added 4 g of synthetic hydrated calcium silicate (obtained from Advanced Minerals Corporation, Lompoc, Calif., USA), and the slurry mixed for approximately 30 min at 20° C. The residue was removed by pressure filtering (i.e., through a coarse cellulose Cuno® CPX-01A depth filter pad, at 20° C. with a pressure of 5–10 psi, 35–70 kPa). The filtrate was collected and assayed for total cholesterol content using a commercially available diagnostic kit (Kit 352-20 from Sigma Chemical Company®). Briefly, an enzymatic, calorimetric, endpoint method is employed in which cholesterol esters are converted to cholesterol; cholesterol is converted to cholest-4-en-one producing hydrogen peroxide as a byproduct; and the hydrogen peroxide causes the formation of quinoneimine dye, which is detected spectrophotometrically by measuring absorbance at 500 nm. Data for the untreated (i.e., control) and treated samples are summarized in Table 4. Treatment with synthetic hydrated calcium silicate effected an approximately 50–85% reduction in total cholesterol content.

TABLE 4

| | Total Cholesterol Content (mg/dL) | |
|---|---|---|
| Sample | Untreated Serum | Treated Serum |
| Serum 1 | 185.7 | 36.4 |
| Serum 2 | 170 | 85 |
| Serum 3 | 304 | 43 |

Example 4
Isolation and Purification of Human Coagulation Factor IX

This example demonstrates the use of SHAES as a capture agent for the harvest and purification of blood coagulant Factor IX.

A sample of Cohn Fraction IV-1 centrifuged precipitate, obtained using standard methods, was dissolved in normal saline solution (i.e., 0.9% NaCl in $H_2O$) using a ratio of 1 gram precipitate per 10 mL of saline solution. The pH of the resulting solution was adjusted to 6.0 with the addition of 1 N NaOH. To a 55 mL aliquot of the resulting solution was added 1 gram (i.e., 0.018 g/mL) of hydrated calcium silicate (obtained from Advanced Minerals Corporation, Lompoc, Calif., USA), and the slurry mixed for 30 min at 20° C. The slurry was then centrifuged in a Beckman® J6B swinging bucket rotor at 1000 rpm for 10 min at 20° C. The centrifuged pellet (approximately 1.0 gram) was suspended in a 0.1 M sodium citrate solution to elute the bound material. The suspension (about 24 mL) was clarified by passing through a 0.2 micron Durapore® filter (from Millipore®) and collecting the harvest filtrate. The harvest filtrate was assayed for Factor IX using the well known activated partial thromboplastin time (APTT) clotting assay. Briefly, commercially available APTT reagent and calcium chloride are added to the plasma fraction, and the time required to form a clot determined. Factor IX deficient plasma is used as a control. The data are summarized in Table 5. Use of the SHAES as a capture material to isolate and/or purify the Factor IX permitted a 30% increase in concentration.

TABLE 5

| Sample | Amount of Factor IX Detected | Recovery (%) |
|---|---|---|
| Dissolved Cohn Fraction IV-1 Precipitate | 0.9 units/mL × 55 mL = 49.5 units | 100 |
| Harvest Filtrate | 1.19 units/mL × 24 mL = 28.6 units | 58 |

REFERENCES

Bottoms, R. R., et al., 1951, U.S. Pat. No. 2,539,397.
Burstein, M. et al., 1957, *J. Physiol. (Paris)*, Vol. 49, p. 83.
Carlson, T., 1991, Principles of Transfusion Medicine. E. C. Rossi, T. L. Simon, G. S. Moss, eds. Williams and Wilkins, Baltimore, Md.
Celite, 1991, "Functional Fillers for Industrial Applications," publication number FF-396 November 1991, Celite Corporation, Lompoc, Calif., USA.
Cohn et al., 1946, *J. Am. Chem. Soc.,* 1946, Vol. 68, pp. 459–475.
Converse, C. A. et al., 1992, ed., *Lipoprotein Analysis: A Practical Approach,* IRL Press.
Curling, J. M., 1980, editor, *Methods of Plasma Protein Fractionation,* Academic Press. Denton, D. A., 1993, U.S. Pat. No. 5,252,762.
Drohan, W. N. et al., 1994, *Scientific Basis of Transfusion Medicine: Implications for Clinical Practice,* K. Anderson and P. Ness, eds. W.B. Saunders Company, Philadelphia, Pa.
Duensing, W. J., et al., 1978, U.S. Pat. No. 4,112,129.
Dwyer, J. M., 1992, "Manipulating the immune system with immune globulin," *N. Engl. J. Med. Vol.* 326, pp. 107–116.
Guyton, A. C., 1991, *Textbook of Medical Physiology:* eighth edition. W.B. Saunders Company, Philadelphia, Pa.
Handin, R. I, et al., 1995, editors, *Blood Principles and Practice of Hematology,* Lippincott, Philadelphia.
Lauck, R. M., et al., 1983, U.S. Pat. No. 4,399,164.
Lawrence, D. P., et al., 1996, editors, *Clinical Practice of Transfusion Medicine, Third Edition,* Churchill Livingston, N.Y.
Lennarz, W. J., 1980, editor, *The Biochemistry of Glycoproteins and Proteoglycans,* Plenum Press.

Putnam, F. W., 1975–1987, editor, *The Plasma Proteins: Structure, Function and Genetic Control*, Volumes 1–5, Academic Press, 1975, 1975, 1977, 1984, and 1987.

Riede, R. G., 1963, U.S. Pat. No. 3,099,626.

Taylor, H. F. W., 1964, editor, *The Chemistry of Cements*, Academic Press.

Walborg, E. F., 1978, editor, *Glycoproteins and Glycolipids in Disease Processes*, Amer. Chem. Soc.

What is claimed is:

1. A method for the selective separation of an organic component from a biological fluid selected from the group consisting of bodily fluids, cell culture fluids, cell lysate fluids, and culture media fluids, said biological fluid comprising said organic component, said method comprising the step of contacting said biological fluid with a synthetic hydrated calcium silicate.

2. A method according to claim 1, comprising the steps of:
   (a) contacting said biological fluid with the synthetic hydrated calcium silicate, thereby forming (i) a residue comprising said synthetic hydrated calcium silicate residue and said organic component, and (ii) remaining fluid; and
   (b) separating said residue from said remaining fluid.

3. A method according to claim 2, wherein said biological fluid further comprises a second organic component, said method comprising the steps of:
   (a) contacting said biological fluid with the synthetic hydrated calcium silicate, thereby forming (i) a residue comprising said synthetic hydrated calcium silicate residue and said organic component, and (ii) remaining fluid comprising said second organic component; and
   (b) separating said residue from said remaining fluid.

4. A method according to claim 2, comprising the steps of:
   (a) contacting said biological fluid with the synthetic hydrated calcium silicate, thereby forming (i) a residue comprising said synthetic hydrated calcium silicate residue and said organic component, and (ii) remaining fluid;
   (b) separating said residue from said remaining fluid; and
   (c) eluting said organic component from said residue.

5. A method for the selective separation of an organic mammalian blood component from a mammalian blood fluid comprising said organic mammalian blood component, said method comprising the step of contacting said mammalian blood fluid with a synthetic hydrated calcium silicate.

6. A method according to claim 5, comprising the steps of:
   (a) contacting said mammalian blood fluid with the synthetic hydrated calcium silicate, thereby forming (i) a residue comprising said synthetic hydrated calcium silicate residue and said organic mammalian blood component, and (ii) remaining fluid; and
   (b) separating said residue from said remaining fluid.

7. A method according to claim 6, wherein said mammalian blood fluid comprises mammalian blood plasma fluid.

8. A method according to claim 6, wherein said organic mammalian blood component comprises lipoprotein.

9. A method according to claim 6, wherein said organic mammalian blood component comprises triacylglycerol.

10. A method according to claim 6, wherein said organic mammalian blood component comprises cholesterol or a cholesteryl ester.

11. A method according to claim 6, wherein said organic mammalian blood component comprises phospholipid.

12. A method according to claim 6, wherein said organic mammalian blood component comprises glycolipid.

13. A method according to claim 6, wherein said organic mammalian blood component comprises glycoprotein.

14. A method according to claim 6, wherein the ratio of said synthetic hydrated calcium silicate to said mammalian blood fluid is 0.001 to 0.05 g/mL.

15. A method for the selective separation of an organic mammalian blood component from a mammalian blood fluid comprising said organic mammalian blood component and a second organic mammalian blood component, said method comprising the steps of:
   (a) contacting said mammalian blood fluid with a synthetic hydrated calcium silicate, thereby forming (i) a residue comprising said synthetic hydrated calcium silicate residue and said organic mammalian blood component, and (ii) remaining fluid comprising said second organic mammalian blood component;
   (b) separating said residue from said remaining fluid.

16. A method according to claim 15, wherein said mammalian blood fluid comprises mammalian blood plasma fluid.

17. A method according to claim 15, wherein said second organic mammalian blood component is a mammalian blood protein.

18. A method according to claim 15, wherein said organic mammalian blood component comprises lipoprotein and said second organic mammalian blood component is a mammalian blood protein.

19. A method according to claim 15, wherein said organic mammalian blood component comprises triacylglycerol and said second organic mammalian blood component is a mammalian blood protein.

20. A method according to claim 15, wherein said organic mammalian blood component comprises cholesterol or a cholesteryl ester and said second organic mammalian blood component is a mammalian blood protein.

21. A method according to claim 15, wherein said organic mammalian blood component comprises phospholipid and said second organic mammalian blood component is a mammalian blood protein.

22. A method according to claim 15, wherein said organic mammalian blood component comprises glycolipid and said second organic mammalian blood component is a mammalian blood protein.

23. A method according to claim 15, wherein said organic mammalian blood component comprises glycoprotein and said second organic mammalian blood component is a mammalian blood protein.

24. A method according to claim 15, said second organic mammalian blood component comprises $\alpha 1$-proteinase inhibitor.

25. A method according to claim 15, wherein the ratio of said synthetic hydrated calcium silicate to said mammalian blood fluid is 0.001 to 0.05 g/mL.

26. A method for the selective separation of an organic mammalian blood component from a mammalian blood fluid comprising said organic mammalian blood component, said method comprising the steps of:
   (a) contacting said mammalian blood fluid with a synthetic hydrated calcium silicate, thereby forming (i) a residue comprising said synthetic hydrated calcium silicate residue and said organic mammalian blood component, and (ii) remaining fluid;
   (b) separating said residue from said remaining fluid; and
   (c) eluting said organic mammalian blood component from said residue.

27. A method according to claim 26, wherein said mammalian blood fluid comprises mammalian blood plasma fluid.

28. A method according to claim 26, wherein said organic mammalian blood component is a mammalian blood protein.

29. A method according to claim 26, wherein said organic mammalian blood component is an apolipoprotein.

30. A method according to claim 26, wherein said organic mammalian blood component is a coagulation factor.

31. A method according to claim 26, wherein said organic mammalian blood component is a coagulation Factor IX.

32. A method according to claim 26, wherein the ratio of said synthetic hydrated calcium silicate to said mammalian blood fluid is 0.001 to 0.05 g/mL.

* * * * *